US00PP24692P2

(12) United States Plant Patent
Jones

(10) Patent No.: US PP24,692 P2
(45) Date of Patent: Jul. 22, 2014

(54) ***SALVIA* PLANT NAMED 'SCAPU14-0'**

(50) Latin Name: *Salvia farinacea*
Varietal Denomination: SCAPU14-0

(76) Inventor: Steve Jones, Santa Monica, CA (US)

( * ) Notice: Subject to any disclaimer, the term of this patent is extended or adjusted under 35 U.S.C. 154(b) by 97 days.

(21) Appl. No.: 13/573,448

(22) Filed: Sep. 14, 2012

(51) Int. Cl.
*A01H 5/00* (2006.01)

(52) U.S. Cl.
USPC ..... Plt./475; Plt./263.1

(58) Field of Classification Search
USPC ..... Plt./263.1, 475
See application file for complete search history.

*Primary Examiner* — Susan McCormick Ewoldt
(74) *Attorney, Agent, or Firm* — Cassandra Bright

(57) ABSTRACT

A new and distinct *Salvia* cultivar named 'SCAPU14-0' is disclosed, characterized by distinctive dark-violet-blue flowers, a compact plant habit, and early flowering. The new variety is a *Salvia*, normally produced as an outdoor garden or container plant.

2 Drawing Sheets

Latin name of the genus and species: *Salvia farinacea*.
Variety denomination: 'SCAPU14-0'.

BACKGROUND OF THE INVENTION

The new cultivar is the product of a planned breeding program. Seed from open pollinated, unpatented, unnamed *Salvia farinacea* plants was planted, and the resulting seedlings evaluated for interesting characteristics. The inventor, Steve Jones selected the new variety in September 2009, at a commercial greenhouse in Oxnard, Calif.

Asexual reproduction of the new cultivar 'SCAPU14-0' by vegetative cuttings was first performed at the end of 2009, at a commercial greenhouse in Oxnard, Calif. and has shown that the unique features of this cultivar are stable and reproduced true to type on successive generations. First commercial sales of the variety took place in October of 2011.

SUMMARY OF THE INVENTION

The cultivar 'SCAPU14-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SCAPU14-0' These characteristics in combination distinguish 'SCAPU14-0' as a new and distinct *Salvia* cultivar:

1. Compact plant habit.
2. Dark Violet-Blue flowers.
4. Early flowering.

PARENT COMPARISON

Plants of the new cultivar 'SCAPU14-0' are similar to plants of the parent varieties of *Salvia farinacea* in most horticultural characteristics, however, plants of the new cultivar 'SCAPU14-0' are shorter and produce a much darker colored flower.

COMMERCIAL COMPARISON

Plant of the new cultivar are best compared to the commercial variety *Salvia farinacea* 'CATHEDRAL SKY BLUE,' U.S. Plant Pat. No. 20,929. Plants are similar in most horticultural characteristics, however, plants of 'SCAPU14-0' produce much darker colored flowers.

BRIEF DESCRIPTION OF THE PHOTOGRAPHS

Figure 1:
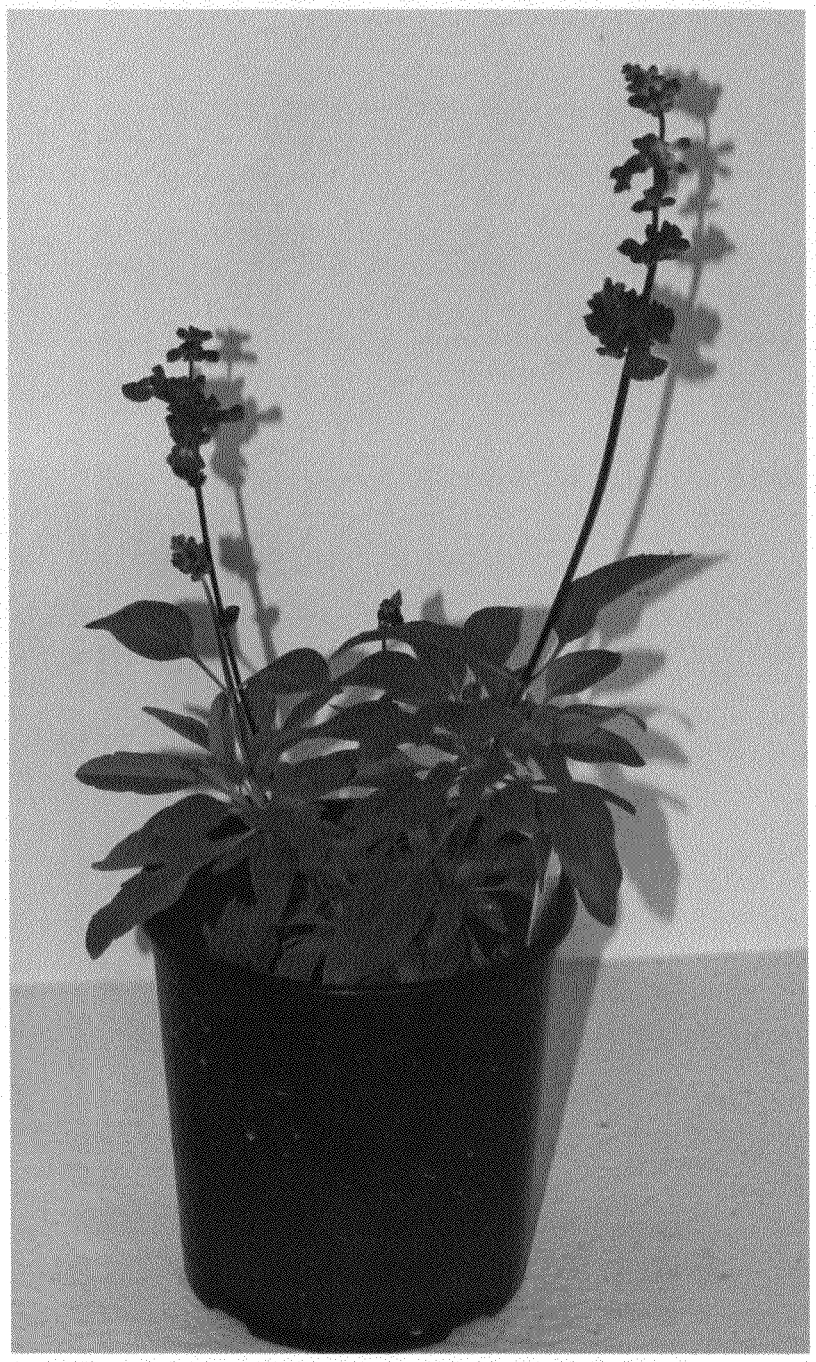

The accompanying photograph in FIG. 1 illustrates in full color a typical plant of 'SCAPU14-0' grown in a greenhouse, in Oxnard, Calif., in a commercial 1 gallon container. Age of the plant photographed is approximately 10 weeks from an unrooted cutting.

Figure 2:
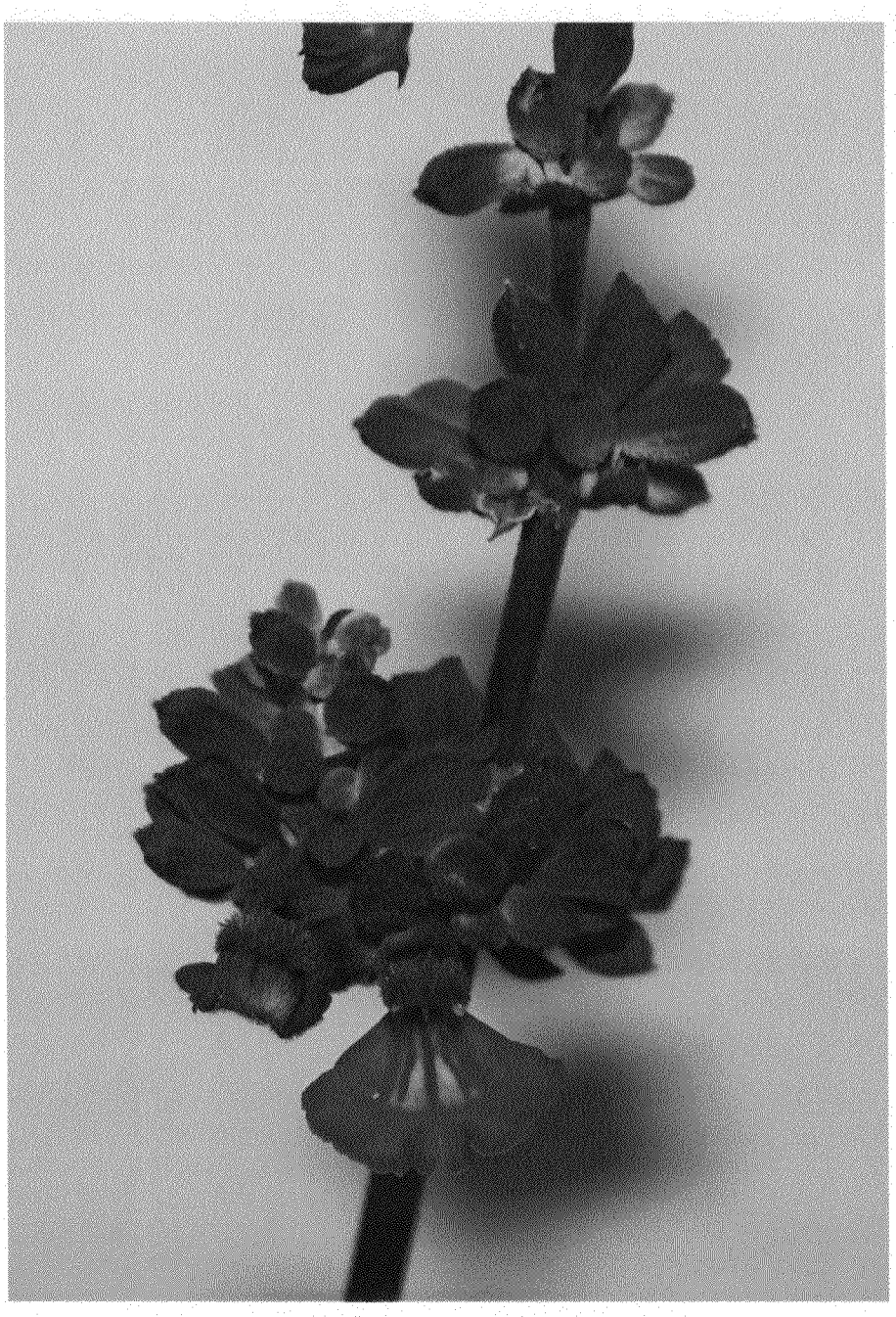

FIG. 2 illustrates in full color a typical inflorescence of 'SCAPU14-0'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'SCAPU14-0' plants grown in a greenhouse in Oxnard, Calif. The growing temperature ranged from 20° C. to 28° C. The greenhouse is un-shaded, giving bright, normal sunlight conditions. Measurements and numerical values represent averages of typical plant types.

Botanical classification: *Salvia farinacea* 'SCAPU14-0'.

PROPAGATION

Time to initiate roots: About 5-8 days at approximately 25° C.
Root description: Fine, densely fibrous.
Time to produce a rooted cutting: About 21 days at 25° C.

PLANT

Growth habit: Upright annual.
Pot size of plant described: 4 inch pot.

Height: Approximately 32 cm to top of foliage. Approximately 49 cm to top of flowering plane. Measured from soil level of pot.
Plant spread: Approximately 28 cm.
Growth rate: Rapid.
Branching characteristics: Free-branching, Approximately 4 primary branches.
Length of primary lateral branches: Approximately 20 cm.
Diameter of lateral branches: Approximately 0.5 cm.
Quantity of lateral branches: About 12.
Characteristics of primary lateral branches:
*Form*.—Round, deeply ridged.
*Color*.—Near RHS Green 143C with infrequent stripes of Greyed-Purple N186A.
*Texture*.—Densely pubescent.
*Strength*.—Moderately strong, somewhat flexible.
Internode length: Average 5.5 cm.
Age of plant described: Approximately 10 weeks from an unrooted cutting.

FOLIAGE

Leaf:
*Arrangement*.—Opposite.
*Quantity*.—Approximately 18 per main branch.
*Average length*.—Approximately 8.2 cm.
*Average width*.—Approximately 1.7 cm.
*Shape of blade*.—Lanceolate.
*Apex*.—Acute.
*Base*.—Attenuate.
*Attachment*.—Stalked.
*Margin*.—Nearly entire, with infrequent dentations.
*Texture of top surface*.—Matte.
*Texture of bottom surface*.—Slightly pubescent.
*Color*.—Young foliage upper side: Near RHS Green 137B. Young foliage under side: Near RHS Green 138A. Mature foliage upper side: Near RHS Green 137B. Mature foliage under side: Near RHS Green 138A.
*Venation*.—Type: Pinnate. Venation color upper side: Near RHS Green 143C. Venation color under side: Near RHS Yellow-Green 145B.
*Petiole*.—Average Length: Approximately 2.2 cm. Diameter: Approximately 0.1 cm. Color: Near Green 138C.

FLOWER

Natural flowering season: Begins flowering between 6 and 7 weeks from planting a rooted cutting. Flowering continues from early Spring through late Summer.
Inflorescence type and habit: Flowers arranged in verticillasters on spikes.
Flower longevity on plant: Individual flowers last 5 days on the plant. Each spike lasts approximately 6 weeks with flowers.
Quantity of flowers: About 24 buds and 28 fully opened flowers per lateral branch, at one time.
Inflorescence size:
*Diameter*.—Approximately 3.0 cm.
*Height*.—Approximately 15.0 cm.
Peduncle:
*Length*.—Average 11.5 cm cm.
*Diameter*.—0.4 cm.
*Color*.—Near RHS Violet-Blue 93A.
*Orientation*.—Upright, straight.
*Strength*.—Strong.
*Texture*.—Pubescent.
Corolla:
*Petal arrangement*.—The corolla is sympetalous and typically bilabiate with 2 small, highly fused lobes forming an upper lip and 3 larger highly fused lobes forming a lower lip.
*Margin*.—Nearly entire, slightly scalloped.
*Tip shape*.—Upper lip tip retuse, lower lip tip rounded with scallops.
*Length*.—Upper lip Approximately 0.6 cm, lower lip Approximately 1.0 cm.
*Width*.—Upper lip Approximately 0.4 cm, lower lip Approximately 1 cm.
*Petal quantity*.—One upper lip and one lower lip with three lobes. Upper lips are entirely fused at base.
*Texture*.—Upper lip is highly pubescent. Lower lip is smooth and hairless.
*Aspect*.—75 to 90° to stem.
*Petaloids*.—Not present.
Color:
*Petals*.—Lower lip: When opening: Upper surface: Near RHS Violet-Blue 93A. Lower surface: Near RHS Violet-Blue 93B, along margin. Interior Violet-Blue 94D. Fully opened: Upper surface: Near RHS Violet-Blue N89B. Lower surface: Near RHS along margin Violet-Blue N89A, interior Near RHS Violet-Blue 91A. Fading: Upper surface: Near RHS Violet-Blue N89A, blotch at base Near RHS White N155A. Lower surface: Near RHS along margin Violet-Blue 93A, interior Near RHS 94C.
Color:
*Petals*.—Upper Lip: When opening: Upper surface: Near RHS Violet-Blue 93A. Lower surface: Near RHS Violet-Blue 93A, along margin. Interior Violet-Blue 92C. Fully opened: Upper surface: Near RHS Violet-Blue 93A. Lower surface: Near RHS Violet-Blue 93A, along margin. Interior Violet-Blue 92C. Fading: Upper surface: Near RHS Violet-Blue 93A. Lower surface: Near RHS Violet-Blue 93A, along margin. Interior Violet-Blue 92C.
Bud:
*Shape*.—Ovoid.
*Length*.—Approximately 0.5 cm.
*Diameter*.—Approximately 0.3 cm.
*Color*.—Near RHS Violet-Blue 93A, base Violet-Blue 92C.
Calyx:
*Length*.—Approximately 0.6 cm.
*Diameter*.—Approximately 0.5 cm.
*Shape*.—Tubular.
Sepals:
*Shape*.—Quantity per flower: 2, fused to form a tube.
*Length*.—Approximately 0.6 cm.
*Width*.—Approximately 0.5 cm.
*Margin*.—Entire.
*Texture*.—Pubescent.
*Calyx tube color*.—Immature: Near RHS Violet-Blue N89A. Mature: Near RHS violet-Blue 92D,, strongly flushed Violet-Blue N92C.
Bracts:
*Quantity*.—2 at the base of each verticillaster.
*Shape*.—Narrow Deltoid.
*Tip*.—Accuminate.
*Texture*.—Pubescent.

*Length*.—Approximately 1.5 cm.

*Width*.—Approximately 0.6 cm.

*Color*.—Upper surface: Near RHS Greyed-Purple N186B. Lower surface: Near RHS Gree138C, veins Violet-Blue N92A.

Persistence: Non-persistent.

Fragrance: Very faint fragrance, non aromatic *Salvia*.

REPRODUCTIVE ORGANS

Stamens:

*Number*.—2.

*Filament length*.—Approximately 0.6 cm.

*Filament color*.—Near RHS Violet-Blue 92D.

Anthers:

*Shape*.—Very narrowly elliptic.

*Length*.—Approximately 1 mm.

*Color*.—Near RHS Violet-Blue N92A.

*Pollen*.—Pollen production not observed.

Pistil:

*Number*.—1.

*Length*.—Approximately 1.1 cm.

*Style*.—Length: Approximately 0.9 cm. Color: Near RHS N155A.

*Stigma*.—Shape: Forked, curled. Color: Near RHS Violet-Blue N92B. Ovary color: Near RHS Green-White 157A.

OTHER CHARACTERISTICS

Seeds and fruits: Not observed to date.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'SCAPU14-0' as herein illustrated and described.

* * * * *